(12) United States Patent
Singh et al.

(10) Patent No.: US 11,680,041 B1
(45) Date of Patent: Jun. 20, 2023

(54) PROCESSES FOR PRODUCING HIGH-PURITY N,N-DIALKYL PERFLUOROALKYLSULFONAMIDE

(71) Applicant: SES Holdings Pte. Ltd., Singapore (SG)

(72) Inventors: Rajendra P. Singh, Woburn, MA (US); Hong Gan, Woburn, MA (US); Qichao Hu, Arlington, MA (US)

(73) Assignee: SES Holdings Pte. Ltd., Singapore (SG)

( * ) Notice: Subject to any disclaimer, the term of this patent is extended or adjusted under 35 U.S.C. 154(b) by 0 days.

(21) Appl. No.: 18/074,587

(22) Filed: Dec. 5, 2022

Related U.S. Application Data

(60) Provisional application No. 63/286,642, filed on Dec. 7, 2021.

(51) Int. Cl.
*H01M 4/02* (2006.01)
*C07C 311/09* (2006.01)

(52) U.S. Cl.
CPC .................. *C07C 311/09* (2013.01)

(58) Field of Classification Search
CPC ...................................... H01M 4/02
See application file for complete search history.

(56) References Cited

U.S. PATENT DOCUMENTS

| | | |
|---|---|---|
| 2021/0053913 A1 | 2/2021 | Zhou et al. |
| 2021/0238142 A1 | 8/2021 | Johnson |

FOREIGN PATENT DOCUMENTS

| | | |
|---|---|---|
| CN | 112679392 A | 4/2021 |
| CN | 112724047 A | 4/2021 |
| CN | 112760672 A | 5/2021 |
| IN | 356764 A | 1/2021 |

OTHER PUBLICATIONS

Sartori ("Electrochemical synthesis of New N,N-bis(trifluoromethyl)perfluoroalkanesulphonamides" Journal of Fluorine Chemistry 75 pp. 157-161, 1995).*

* cited by examiner

*Primary Examiner* — Jacob B Marks
(74) *Attorney, Agent, or Firm* — Downs Rachlin Martin PLLC

(57) ABSTRACT

Processes for producing a N,N-dialkyl perfluoroalkyl-sulfonamide product of the formula $R_f-S(O)_2-NR_aR_b$ (I) in which $R_f$ represents fully or partially fluorinated alkyl groups with carbon 1 to 12 and $R_a$ and $R_b$ represents linear or branched or cyclic alkyl, alkene or alkyne groups with carbon 1 to 12, wherein $R_a=R_b$ or $R_a \neq R_b$. In some embodiments, a reaction proceeds by contacting a perfluoroalkylsulfonyl halide of the formula: $X-S(O)_2-R_f$ (II), in which X represents F, Cl, Br or I, with dialkylamine of the formula $HNR_aR_b$, under conditions sufficient to produce the desired N,N-dialkyl perfluoroalkylsulfonamide product of Formula I. In some embodiments, the reaction is carried out using a solvent of Formula I.

27 Claims, No Drawings

PROCESSES FOR PRODUCING HIGH-PURITY N,N-DIALKYL PERFLUOROALKYLSULFONAMIDE

RELATED APPLICATION DATA

This application claims the benefit of priority of U.S. Provisional Patent Application Ser. No. 63/286,642, filed Dec. 7, 2021, and titled "Process For Producing High-purity N, N-Dialkyl Perfluoroalkyl Sulfonamide," which is incorporated by reference herein in its entirety.

FIELD OF THE DISCLOSURE

The present disclosure generally relates to N,N-dialkyl perfluoroalkylsulfonamide. More particularly, the present disclosure is directed to processes for producing high-purity N,N-dialkyl perfluoroalkylsulfonamide.

BACKGROUND

Incorporation of fluorine into a chemical compound often results in a significant change in the physical and chemical properties of the compound, such as lowering the melting point, increasing the thermal stability, and making it non-flammable. Some fluorine-containing compounds have wider electrochemical stability windows and are useful in electrochemical energy storage devices, such as batteries and electric double-layer capacitors (EDLCs).

At present, N,N-dimethyl trifluoromethanesulfonamide ($CF_3S_2NMe_2$) is not commercially available in high purity and in large quantity due to synthesis difficulties.

Synthesis of $CF_3SO_2NMe_2$ has been reported by refluxing trifluoromethanesulfonyl fluoride ($CF_3SO_2F$) and dimethylamine (($CH_3$)$_2$NH) in carbon tetrachloride ($CCl_4$). Carbon tetrachloride is carcinogenic and has been banned from use. Also, $CF_3SO_2F$ is very toxic and the produced HF byproduct is highly corrosive. (Lit. Anorganische Chemie, Organische Chemie, Biochemie, Biophysik, Biologie (1970), 25(3), 252-4).

Synthesis of $CF_3SO_2NMe_2$ is reported in a closed system (an autoclave) using $CF_3SO_2F$ and ($CH_3$)$_2$NH. The product was isolated by extraction with ether. In this reaction, use of $CF_3SO_2F$ is very expensive and toxicity is high. The byproduct HF is highly corrosive, and the reaction cannot be carried out in a glass reactor. Ether is also not an optimal solvent due to its ability to generate peroxide.

In another synthesis of $CF_3SO_2NMe_2$ (Chem 5, 2019, 10, 2630-26410), 2 M dimethylamine in tetrahydrofuran (THF) was reacted with $CF_3SO_2Cl$ containing triethylamine as an HCl scavenger using dichloromethane as a solvent. The reaction temperature was −78° C. Again, dichloromethane is corrosive, the final product was isolated by double distillation, and the reported boiling point is not correct for high-purity $CF_3SO_2NMe_2$.

Synthesis of $CF_3SO_2NMe_2$ was reported (French Patent No. FR 806 383; German Patent No. DE 667 544; U.S. Pat. No. 2,130,038) by the reaction of $CF_3SO_2NH_2$ with $CH_3I$ in THF in the presence of lithium carbonate by refluxing at 40° C. This reaction produced a yellow product after multiple distillations and in low yield.

$CF_3SO_2NMe_2$ has also been prepared (Journal of Fluorine Chemistry (2010), 131(7), 761-766) by the reaction of $CF_3S_2Cl$ with excess dimethylamine at −78° C. in dichloromethane. Yield was <80%. After the usual workup reported in the literature, it has been observed that the final product contained traces of amines and dichloromethane. These impurities made the resulting $CF_3SO_2NMe_2$ unsuitable for use as a solvent for lithium-metal batteries.

Accordingly, there is a need for more friendly and less costly methods of producing high purity $CF_3SO_2NMe_2$.

SUMMARY OF THE DISCLOSURE

In an implementation, the present disclosure is directed to a method of producing an N,N-dialkyl perfluoroalkylsulfonamide product of the formula $R_f$—$SO_2$—$NR_aR_b$ (Formula I) wherein $R_f$ is a perfluorinated alkyl, each $R_a$ and $R_b$ is, independently, an alkyl, and $R_a=R_b$ or $R_a \neq R_b$. The method includes, in the presence of an external reaction solvent of Formula I, contacting a perfluoroalkyl-sulfonyl halide of the formula X—$S(O)_2$—$R_f$, wherein X is a halide, with a dialkylamine of the formula $HNR_aR_b$ under conditions sufficient to produce the N,N-dialkyl perfluoroalkylsulfonamide product of Formula I.

DETAILED DESCRIPTION

The present disclosure provides methods of producing N,N-dialkyl perfluoroalkyl-sulfonamide and derivatives thereof of the formula:

$$R_f\text{—}S(O)_2\text{—}NR_aR_b \qquad (I)$$

by contacting at least one perfluoroalkylsulfonyl halide compound of the formula:

$$X\text{—}S(O)_2\text{—}R_f \qquad (II)$$

with at least one dialkylamine of the formula:

$$HNR_aR_b \qquad (III)$$

(e.g., dimethylamine when $R_a=R_b$=methyl) under conditions sufficient to produce the compound of Formula I, wherein:

$R_f$ is a perfluorinated alkyl;

each of $R_a$ and $R_b$ is, independently, an alkyl, wherein $R_a=R_b$ or $R_a \neq R_b$; and X is a halide.

In some embodiments, this reaction uses a reaction solvent that is the same as the desired reaction product, i.e., the reaction solvent is a compound of Formula I, above, and yield is very high. If the above reaction is carried out without any solvent, the reaction is very violent. Thus, a solvent is needed to dilute the reactants. As noted in the Background section above, synthesis processes in literature uses THF or dichloromethane, but these solvents are retained in the final products. Consequently, the reaction product needs severe purification, which lowers the yield. When using the desired product of the above reaction, i.e., the compound of Formula I, as the diluting solvent, the issue with unwanted contaminating solvent in the desired product is avoided because the solvent is the same compound as the desired product.

When a compound of Formula I is used as a reaction solvent, for example, as the sole reaction solvent, impurities from other solvents are avoided, leading to high purity product suitable for battery electrolyte applications. In some embodiments in which a compound of Formula I is present as the reaction solvent, the compound is added to the reaction as an external reaction solvent. In some embodiments, an initial external reaction solvent of Formula I may be made using a synthesis of known literature (e.g., Journal of Fluorine Chemistry (2010), 131(7), 761-766)) and then doing extensive purification. In some embodiments, once the new solvent of Formula I is made using a process of the present disclosure, at least some of the new solvent can be used in future syntheses.

Definitions

"Alkyl" refers to a saturated linear monovalent hydrocarbon moiety of one to twelve, typically one to six, carbon atoms or a saturated branched monovalent hydrocarbon moiety of three to twelve, typically three to six, carbon atoms. Alkyl groups can optionally be substituted with an alkoxide (i.e., —$OR^a$, where $R^a$ is alkyl) and/or other functional group(s) that are either protected or non-reactive under a given reaction condition.

The terms "halo," "halogen" and "halide" are used interchangeably herein and refer to fluoro, chloro, bromo, or iodo.

As used herein, the term "optionally substituted" means the group is optionally substituted with one or more substituents that are nonreactive under a given reaction condition.

When describing a chemical reaction, the terms "treating", "contacting", and "reacting" are used interchangeably and refer to adding or mixing two or more reagents under appropriate conditions to produce the indicated and/or the desired product. It should be appreciated that the reaction that produces the indicated and/or the desired product may not necessarily result directly from the combination of two reagents that were initially added, i.e., there may be one or more intermediates that are produced in the mixture that ultimately lead to the formation of the indicated and/or the desired product.

The term "about" when used with a corresponding numeric value refers to ±20% of the numeric value, typically ±10% of the numeric value, often ±5% of the numeric value, and most often ±2% of the numeric value. In some embodiments, the term "about" can be taken as exactly indicating the actual numerical value.

General

As noted in the Background section above, N,N-dimethyl-trifluoromethane-sulfonamide is useful in various applications including as a solvent in electrolytes for electrochemical devices such as batteries (e.g., lithium-metal batteries, among others) and capacitors (e.g., EDLCs, among others). The present disclosure is directed to synthesizing N,N-dimethyl-trifluoromethanesulfonamide and like derivatives, more generally, N,N-dialkyl-perfluoroalkyl sulfonamides. N,N-dimethyl-trifluoromethanesulfonamide, as an example, is hydrolytically stable and has capacity to form a lithium fluoride (LiF) solid-electrolyte interphase (SEI) layer in lithium-metal batteries. There is no large-scale commercial production presently existing due to limited fluorination chemistries suitable for its synthesis.

In some embodiments, this disclosure is directed to synthesizing N,N-dimethyl-trifluoromethanesulfonamide using N,N-dimethylamine and at least one trifluoromethane-sulfonyl halide using an external solvent that is the same as the desired product (here, the N,N-dimethyl-trifluoromethanesulfonamide product). However and as noted above, the process can be generalized to the synthesis of N,N-dialkyl perfluoroalkylsulfonamide of Formula I by contacting at least one perfluoroalkylsulfonyl halide of Formula II with at least one dialkylamine of Formula III.

As also noted above, in some embodiments the only external solvent, or "reaction solvent") used in the synthesis is the same compound as the desired product. In these embodiments, other than the reactants and reaction products, no other organic solvents or materials are used, thus effectively eliminating sources of organic impurities in the final product. In some embodiments, the disclosed chemistry involves a liquid reactant and producing a liquid desired product and dimethylamine hydrochloride as a solid byproduct.

In the present instantiation in which the halide present in the reaction mixture is chlorine, the reaction also produces hydrogen chloride (HCl). For example, when desiring to produce N,N-dimethyl-trifluoromethanesulfonamide, the process of reacting $CF_3SO_2Cl$ with dimethylamine also comprises removing HCl that is produced in the reaction. Typically, the boiling point of HCl is lower than that of product. Therefore, HCl can be removed by simple distillation or evaporation. Generally, by adjusting the condensation temperature, the desired product can be selectively condensed while allowing HCl to be distilled away from the reaction mixture. HCl can also be captured by passing the resulting vapor through another condenser at a temperature that is sufficiently low enough to allow HCl to be captured, typically as a liquid. Alternatively, HCl can be neutralized by contacting with a base.

By conducting the reaction at an ambient (e.g., standard atmospheric) pressure condition, the present inventors have discovered that a high yield of N,N-dimethyl-trifluoromethanesulfonamide was produced using $CF_3SO_2Cl$ and dimethylamine. By precipitating HCl as dimethylamine hydrochloride ($C_2H_8ClN$) generated during the reaction further increases the yield of N,N-dimethyl trifluoromethanesulfonamide in accordance with the Le Chatelier's Principle.

Typically, the reaction temperature is at least −78° C., often at least −40° C., and more often at least 0° C. The present inventors have found that under certain reaction conditions, for example, atmospheric pressure, −50° C. for about 4 hours and then room temperature (about 20° C.) for about 12 hours, reacting $CF_3SO_2Cl$ with excess dimethylamine resulted in formation of N,N-dimethyl trifluoromethanesulfonamide in at least 85% yield, typically in at least 90% yield, often in at least 95% yield and more often in at least 99% yield.

In some embodiments, the reaction conditions comprise atmospheric pressure, such as standard atmospheric pressure. In some embodiments, the reaction is conducted in a continuous stirred tank reactor with continuous $CF_3SO_2Cl$ and dimethylamine feeds. In some embodiments, the dimethylamine hydrochloride byproduct was found to be insoluble in the product solvent and precipitated out right away. This shifted the equilibrium to the right (see, e.g., the reaction equations in the Examples below), thus completing the reaction and giving almost quantitative yield in contrast to the known synthesis reactions.

In some embodiments, each of the perfluoroalkylsulfonyl halide and the dialkylamine is mixed with an external reaction solvent, for example, an external reaction solvent of Formula I, above, to form corresponding perfluoroalkylsulfonyl halide and dialkylamine solutions. In some embodiments, that reactant:solvent ratio, by weight, in each of these solutions is in a range of about 1:0.5 to about 1:2, or any subrange therein. In some embodiments, a reactant:solvent weight ratio of about 1:1 appears to provide good results.

In some embodiments, the dialkylamine solution is added to the perfluoroalkylsulfonyl halide solution to form a mixture, which may then be stirred to promote thorough contact between the perfluoroalkylsulfonyl halide and the dialkylamine. In some embodiments, the temperature of the mixture may be maintained at a lower temperature (e.g., about 0° C. or lower, about −20° C. or lower, about −40° C. or lower, or about −78° C. to about 0° C.) for a first period of time. After the first period of time, the temperature of the mixture may be raised and held at at least one higher temperature (e.g., higher than 0° C., about 5° C. or higher, about 10° C. or higher, about 20° C. or higher, or about standard room temperature) for a second period of time. In some embodiments, the first period of time may be in a range from about 1 hour to about 6 hours, and the second period of time may be in a range from about 4 hours to about 20 hours, among others.

In some embodiments, a byproduct of the reaction is a salt containing a hydrogen halide (X) (e.g., HCl) and some of the dialkylamine. In some embodiments (e.g., when the byproduct is dialkylamine hydrochloride), the salt byproduct can be filtered to provide a filtered solution. The filtered solution can be washed, for example, with pure deionized (DI) water to remove unwanted water-soluble impurities, such as any remaining salt byproduct. When DI water is used, excess DI water is added to the solution and stirred well. The resulting solution may, for example, be placed in a separatory funnel and allowed to separate into two layers. The lower layer is extracted and in some embodiments washed with an acid solution, such as an HCl solution (e.g., a 1 M HCl solution), to make it free from any base. The washed lower-layer solution may be washed again with pure DI water to remove any water-soluble impurities, such as the dialkylamine hydrochloride salt, dried (e.g., over anhydrous sodium sulfate), and filtered. The resulting filtered product may be distilled at a reduced pressure to give the final desired product of Formula I, above.

As those skilled in the art will readily appreciate and as noted above, synthesizing an N,N-dialkyl perfluoroalkylsulfonamide composition of Formula I, above, or derivative of the present disclosure using an external reaction solvent of the same composition has a number of important benefits. These benefits include producing the desired product in a higher yield than a typical conventional synthesis process while simultaneously producing a higher purity desired product with fewer processing steps. The higher yield is due to the fact that when the composition of the external reaction solvent is identical to the desired product, there is no other external solvent, i.e., no solvent of a composition different from the final product, that needs to be removed. When a non-identical solvent is used, the purification process is much more extensive, and the additional purification typically removes some of the desired product along with the contaminants. Regarding the lower number of processing steps, as just noted, more extensive purification needs to be done when the external reaction solvent is different from the desired product. This clearly leads to fewer processing steps needed, which reduces processing costs and processing time.

Additional objects, advantages, and novel features of embodiments of this disclosure will become apparent to those skilled in the art upon examination of the following examples, which are not intended to be limiting but instructive. In the Examples, procedures that are constructively reduced to practice are described in the present tense, and procedures that have been carried out in the laboratory are set forth in the past tense.

EXAMPLES

Example 1-Synthesis of N,N-dimethyl Trifluoromethanesulfonamide

To a dry 3-neck, 2L flask equipped with cold condenser and dropping funnel under argon, dimethylamine (266 g, 5.91 mole) was condensed at −50° C. and mixed with 300 g of anhydrous N,N-dimethyl trifluoromethanesulfonamide obtained from prior synthesis. Trifluoromethanesulfonyl chloride ($CF_3SO_2Cl$) (400 g, 2.37 mole) was taken in a dropping funnel and mixed with 200 g of anhydrous N,N-dimethyl trifluoromethanesulfonamide obtained from prior synthesis. Dropping funnel temperature was maintained to about 10° C. by circulating cold water. Three neck flask temperature was maintained to −50° C., for example, using a bath of an isopropanol and liquid $N_2$ mixture. Dimethylamine solution was added into the $CF_3SO_2Cl$ solution with stirring. Reaction temperature was maintained at −50° C. ±5° C. After complete addition of the dimethylamine solution, the reaction mixture was stirred at −50° C. for 1 hour and the bath was allowed to warm to room temperature in about 3 hours. Reaction was kept at room temperature overnight with stirring (total reaction time 16 hours). Formation of dimethylamine hydrochloride salt was seen as an insoluble byproduct and was removed by filtration. The resulting obtained solution was treated with excess deionized (DI) water and stirred well and then poured into a separatory funnel. Two layers formed, and the desired product was in lower layer. The portion of the reaction product in the lower layer was washed several times with 1 M HCl solution to make it free from any base. Since the product in this reaction was the same as the initially added external reaction solvent (i.e., N, N-dimethyl trifluoromethanesulfonamide), it was washed with pure DI water to remove any water-soluble impurities, such as dimethylamine hydrochloride byproduct and was dried over anhydrous sodium sulfate and filtered. It was distilled at reduced pressure to give a clear colorless liquid. Yield: 95%. b. p. 42° C./12 mm), $^1H$ NMR: δ3.07 (s, 6H). $^{19}F$ NMR δ−75.0 (s, 3F). Following is an equation representing the reaction of Example 1.

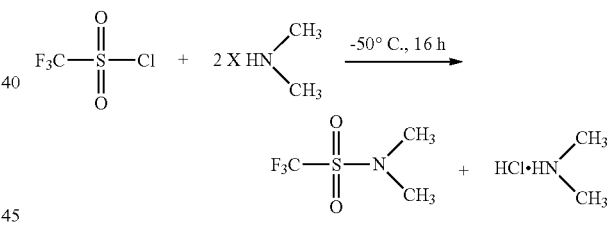

Example 2-Synthesis of N,N-dimethyl Trifluoromethanesulfonamide

To a dry 3-neck, 2 L flask equipped with cold condenser and dropping funnel under argon, dimethylamine (110 g, 2.44 mole) was condensed at −45° C. and mixed with 300 g of anhydrous N,N-dimethyl trifluoromethanesulfonamide obtained from prior synthesis followed by addition of 246g, 2.44 mol) of triethylamine. Trifluoromethanesulfonyl chloride ($CF_3SO_2Cl$) (400 g, 2.37 mole) was taken in a dropping funnel and mixed with 200 g of anhydrous N,N-dimethyl trifluoromethanesulfonamide obtained from prior synthesis. Dropping funnel temperature was maintained to about 10° C. by circulating cold water. Three neck flask temperature was maintained to −45° C., for example, using a bath of an isopropanol and liquid N2 mixture. Dimethylamine solution was added into the $CF_3SO_2Cl$ solution with stirring. Reaction temperature was maintained at −45° C.+5° C. After complete addition of the trifluoromethane-sulfonyl chloride solution, the reaction mixture was stirred at −45° C. for 1 hour, and the bath was allowed to warm to room temperature in about 3 hours. Reaction was kept at room temperature overnight with stirring (total reaction time 16 hours). Formation of dimethylamine hydrochloride salt was seen as an insoluble byproduct and was removed by filtration. The resulting obtained solution was treated with excess DI water and stirred well and then poured into a separatory funnel. Two layers formed, and the desired product was in lower layer. The portion of the reaction product in the lower layer was washed several times with 1 M HCl solution to make it free from any base. Since the product in this reaction was the same as the initially added external reaction solvent (i.e., N,N-dimethyl trifluoromethanesulfonamide), it was washed with pure DI water to remove any water-soluble impurities, such as trirthylamine hydrochloride byproduct and was dried over anhydrous sodium sulfate and filtered. It was distilled at reduced pressure to give a clear colorless liquid. Yield: 95%. b.p. 42° C./12 mm), $^1$H NMR: δ3.07 (s, 6H). 19F NMR δ-75.0 (s, 3F). Following is an equation representing the reaction of Example 2.

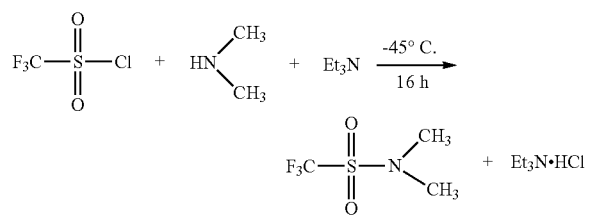

Example 3-Synthesis of N,N-diethyl Trifluoromethanesulfonamide

To a dry 3-neck, 2L flask equipped with cold condenser and dropping funnel under argon, diethylamine (292 g, 4 mole) was condensed at −50° C. and mixed with 200 g of anhydrous N,N-diethyl trifluoromethanesulfonamide obtained from prior synthesis. Trifluoromethanesulfonyl chloride (CF$_3$SO$_2$Cl) (269 g, 1.6 mole) was taken in the dropping funnel and mixed with 100 g of anhydrous N,N-diethyl trifluoromethanesulfonamide obtained from prior synthesis. Dropping funnel temperature was maintained to about 10° C. by circulating cold water. Three neck flask temperature was maintained to −50° C. using a bath of an isopropanol and liquid N$_2$ mixture. Diethylamine solution was added into the CF$_3$SO$_2$Cl with stirring. Reaction temperature was maintained at −50° C. ±5° C. After complete addition of the diethylamine solution, the reaction mixture was stirred at −50° C. for 1 hour and bath was allowed to warm to room temperature in about 3 hours. Reaction was kept at room temperature overnight with stirring (total reaction time 16 hours). Formation of diethylamine hydrochloride salt was seen as an insoluble byproduct and was removed by filtration. The resulting obtained solution was treated with excess DI water and stirred well and then poured into separatory funnel. Two layers formed, and the desired product was in lower layer. The portion of the reaction product in the lower layer was washed several times with 1 M HCl solution to make free from any base. Since the product in this reaction was the same as the initially added external reaction solvent (i.e., N,N-diethyl trifluoromethane-sulfonamide), it was washed with pure DI water to remove any water-soluble impurities and was dried over anhydrous sodium sulfate and filtered. It was distilled at reduced pressure to give a clear colorless liquid. Yield: 92% $^1$H NMR: δ3.45 (q, 4H), 1.25 (t, 6H). $^{19}$F NMR δ−77.0 (s, 3F). Following is an equation representing the reaction of Example 3.

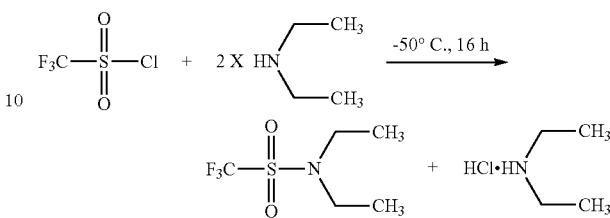

Example 4-Synthesis of N,N-dimethyl Pentafluoroethanesulfonamide

To a dry 3-neck, 2L flask equipped with cold condenser and dropping funnel under argon, dimethylamine (133 g, 2.95 mole) was condensed at −50° C. and mixed with 150 g of anhydrous N,N-dimethyl pentafluoroethanesulfonamide obtained from prior synthesis. Pentafluoroethanesulfonyl chloride (257.8 g, 1.18 mole) was taken in the dropping funnel and mixed with 100 g of anhydrous N,N-dimethyl pentafluoroethanesulfonamide obtained from prior synthesis. Dropping funnel temperature was maintained to about 10° C. by circulating cold water. Three neck flask temperature was maintained to −50° C. using a bath of an isopropanol and liquid N$_2$ mixture. Dimethylamine solution was added into the CF$_3$CF$_2$SO$_2$Cl solution with stirring. Reaction temperature was maintained at −50° C. ±5° C. After complete addition of the dimethylamine solution, the reaction mixture was stirred at −50C for 1 hour and bath was allowed to warm to room temperature in about 3 hours. Reaction was kept at room temperature for overnight with stirring (total reaction time 16 hours). Formation of dimethylamine hydrochloride salt was seen as an insoluble byproduct and was removed by filtration. The resulting obtained solution was treated with excess DI water and stirred well and then poured into separatory funnel. Two layers formed, and the desired product was in lower layer. The portion of the reaction product in the lower layer was washed several times with 1 M HCl solution to make free from any base. Since the product in this reaction was the same as the initially added external reaction solvent (i.e., N,N-dimethyl pentafluoroethanesulfonamide), it was washed with pure DI water to remove any water-soluble impurities and was dried over anhydrous sodium sulfate and filtered. It was distilled at reduced pressure to give a clear colorless liquid. Yield: 90%. Following is an equation representing the reaction of Example 4.

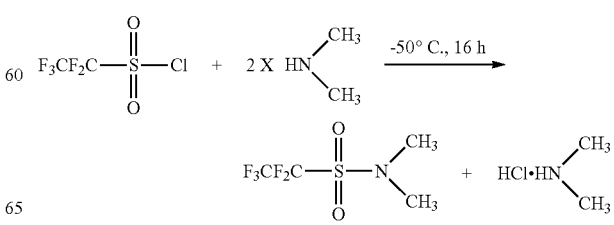

Example 5-Synthesis of morpholino-N-trifluoromethanesulfonamide

To a dry 3-neck, 2 L flask equipped with cold condenser and dropping funnel under argon, morpholine (217.7 g, 2.5 mole) was condensed at −50° C. and mixed with 100 g of anhydrous morpholino-N-trifluoromethanesulfonamide obtained from prior synthesis. Trifluoromethanesulfonyl chloride (CF$_3$SO$_2$Cl) (168.5 g, 1 mole) was taken in the dropping funnel and mixed with 100 g of anhydrous morpholino N-trifluoromethanesulfonamide obtained from prior synthesis. Dropping funnel temperature was maintained to about 10° C. by circulating cold water. Three neck flask temperature was maintained to −50° C. using a bath of isopropanol/dry ice or liquid N$_2$ mixture. Morpholine solution was added into the CF$_3$SO$_2$Cl with stirring. Reaction temperature was maintained at −50° C. ±5° C. After complete addition of the morpholine solution, the reaction mixture was stirred at −50° C. for 1 hour and the bath was allowed to warm to room temperature in about 3 hours. Reaction was kept at room temperature for overnight with stirring (total reaction time 16 hours). Formation of morpholinium hydrochloride salt was seen as an insoluble byproduct and was removed by filtration. The resulting obtained solution was treated with excess DI water and stirred well and then poured into separatory funnel. Two layers formed, and the desired product was in lower layer. The portion of the reaction product in the lower layer was washed several times with 1 M HCl solution to make free from any base. Since the product in this reaction was the same as initially added external reaction solvent (i.e., morpholino N-trifluoromethanesulfonamide), it was washed with pure DI water to remove any water-soluble impurities and was dried over anhydrous sodium sulfate and filtered. It was distilled at reduced pressure to give a clear colorless liquid. Yield: 95%. $^1$H NMR: δ3.75 (t, 4H), 3.51(t, 4H). $^{19}$F NMR δ−75.5 (s, 3F). Following is an equation representing the reaction of Example 5.

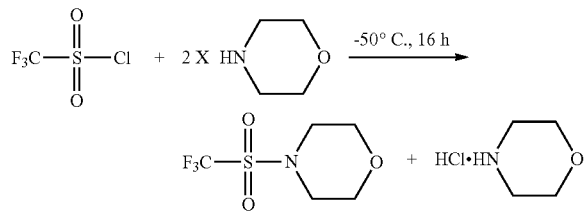

Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments and examples, what has been described herein is merely illustrative of the application of the principles of the present disclosure. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this disclosure.

Exemplary embodiments have been disclosed above and illustrated in the accompanying drawings. It will be understood by those skilled in the art that various changes, omissions and additions may be made to that which is specifically disclosed herein without departing from the spirit and scope of the present disclosure.

What is claimed is:

1. A method of producing an N,N-dialkyl perfluoroalkylsulfonamide product of the formula R$_f$—SO$_2$—NR$_a$R$_b$ (Formula I) wherein R$_f$ is a perfluorinated alkyl, each R$_a$ and R$_b$ is, independently, an alkyl, and R$_a$=R$_b$ or R$_a$ ≠R$_b$, the method comprising:
   in the presence of an external reaction solvent of Formula I, contacting a perfluoroalkyl-sulfonyl halide of the formula X—S(O)$_2$—R$_f$, wherein X is a halide, with a dialkylamine of the formula HNR$_a$R$_b$ under conditions sufficient to produce the N,N-dialkyl perfluoroalkylsulfonamide product of Formula I.

2. The method of claim 1, wherein the contacting is performed without the presence of any solvent not of Formula I.

3. The method of claim 2, wherein the yield of the N,N-dialkyl perfluoroalkylsulfonamide product is at least about 90%.

4. The method of claim 2, wherein the yield of the N,N-dialkyl perfluoroalkylsulfonamide product is at least about 95%.

5. The method of claim 2, wherein the yield of the N,N-dialkyl perfluoroalkylsulfonamide product is at least about 99%.

6. The method of claim 1, further comprising adding the external reaction solvent to create a reactant:solvent ratio, by weight, in a range of about 1:0.5 to about 1:2.

7. The method of claim 6, wherein the reactant:solvent ratio is in a range of about 1:1 to about 1:2.

8. The method of claim 6, wherein the reactant:solvent ratio is about 1:1.

9. The method of claim 1, further comprising, prior to contacting the perfluoroalkylsulfonyl halide with the dialkylamine, creating a solution of the perfluoroalkylsulfonyl halide and a first portion of the external reaction solvent, and creating a solution of the dialkylamine and a second portion of the external reaction solvent, wherein the contacting includes mixing the perfluoroalkylsulfonyl halide solution with the dialkylamine solution.

10. The method of claim 9, wherein each of the perfluoroalkylsulfonyl halide solution and the dialkylamine solution has a reactant:solvent ratio, by weight, in a range of about 1:0.5 to about 1:2.

11. The method of claim 9, wherein each of the perfluoroalkylsulfonyl halide solution and the dialkylamine solution has a reactant:solvent ratio, by weight, in a range of about 1:1 to about 1:2.

12. The method of claim 9, wherein each of the perfluoroalkylsulfonyl halide solution and the dialkylamine solution has a reactant:solvent ratio, by weight, of about 1:1.

13. The method of claim 1, wherein a byproduct of the contacting includes a dialkylamine hydrogen halide, and the method further includes removing at least some of the dialkylamine hydrogen halide.

14. The method of claim 13, wherein removing at least some of the dialkylamine hydrogen halide includes at least one washing with deionized water.

15. The method of claim 14, wherein a washed solution containing the N,N-dialkyl perfluoroalkyl-sulfonamide product, the dialkylamine hydrogen halide, and the deionized water is allowed to separate.

16. The method of claim 15, further comprising creating an acid-washed lower-layer solution by extracting a lower layer of the washed solution and washing the extracted lower layer with an acid solution.

17. The method of claim 16, wherein the acid solution is an HCl solution.

18. The method of claim 16, further comprising washing the acid-washed lower-layer solution with deionized water and then removing the deionized water to obtain the final N,N-dialkyl perfluoroalkylsulfonamide product.

19. The method of claim 13, wherein the dialkylamine hydrogen halide comprises dialkylamine hydrogen chloride.

20. The method of claim 1, wherein the contacting is performed at about standard atmospheric pressure.

21. The method of claim 1, wherein the external reaction solvent, the perfluoroalkylsulfonyl halide, and the dialkyamine for a reaction mixture, and the method further includes mixing the reaction mixture for a time in a range of about 1 hour to about 25 hours.

22. The method of claim 21, further comprising, mixing the reaction mixture in a first time range of about 1 hour to about 6 hours at a first temperature of lower than about −20° C. and then mixing the reaction mixture in a second time range of about 4 hours to about 20 hours at a second temperature of higher than about 0° C.

23. The method of claim 21, wherein the second temperature is about room temperature.

24. The method of claim 1, wherein the N,N-dialkyl perfluoroalkyl-sulfonamide comprises N,N-dimethyl trifluoromethanesulfonamide, the perfluoroalkylsulfonyl halide comprises trifluoromethanesulfonyl chloride, and the dialkylamine comprises dimethylamine.

25. The method of claim 1, wherein the N,N-dialkyl perfluoroalkyl-sulfonamide comprises N,N-diethyl trifluoromethanesulfonamide, the perfluoroalkylsulfonyl halide comprises trifluoromethanesulfonyl chloride, and the dialkylamine comprises diethylamine.

26. The method of claim 1, wherein the N,N-dialkyl perfluoroalkyl-sulfonamide comprises N,N-dimethyl pentafluoroethanesulfonamide, the perfluoroalkylsulfonyl halide comprises pentafluoroethanesulfonyl chloride, and the dialkylamine comprises dimethylamine.

27. The method of claim 1, wherein the N,N-dialkyl perfluoroalkyl-sulfonamide comprises morpholino-N-trifluoromethanesulfonamide, the perfluoroalkylsulfonyl halide comprises trifluoromethanesulfonyl chloride, and the dialkylamine comprises morpholine.

\* \* \* \* \*